United States Patent
Estivill Palleja et al.

(10) Patent No.: US 6,225,057 B1
(45) Date of Patent: May 1, 2001

(54) DUPLICATIONS OF HUMAN CHROMOSOME 15Q24-25 AND ANXIETY DISORDERS, DIAGNOSTIC METHODS FOR THEIR DETECTION

(75) Inventors: Xavier Estivill Palleja; Monica Gratacos; Marga Nadal; Miguel Angel Pujana; Victor Volpini, all of Barcelona (ES)

(73) Assignee: Palleja, Zavier Estivell, Barcelona (ES)

( * ) Notice: Subject to any disclaimer, the term of this patent is extended or adjusted under 35 U.S.C. 154(b) by 0 days.

(21) Appl. No.: 09/121,546

(22) Filed: Jul. 23, 1998

(51) Int. Cl.[7] .............................. C12Q 1/68; C12P 19/34

(52) U.S. Cl. ............................................... 435/6; 435/91.1

(58) Field of Search ........................................ 435/6, 91.1

(56) References Cited

PUBLICATIONS

Bulbena et al. Lancet, vol. 2, p. 694, 1988.*

\* cited by examiner

*Primary Examiner*—W. Gary Jones
*Assistant Examiner*—Jehanne Souaya
(74) *Attorney, Agent, or Firm*—Ladas & Parry

(57) ABSTRACT

A method for identifying a person at risk for developing an anxiety disorder, said anxiety disorder selected from the group consisting of agoraphobia, social phobia, panic attacks, panic disorders, simple phobia, mood disorders, major depression, schizophrenia, and hypermobility syndrome associated with duplication of a region of the genomic sequence of human chromosome 15q24-25 defined by boundaries D15S925 (proximal end) and DS15S736 (distal end). The method comprises identifying the presence of duplication in the region of the genomic sequence of human chromosome 15q24-25 defined by the boundaries D15S925 (proximal end) and DS15S736 (distal end) in said person.

5 Claims, 6 Drawing Sheets

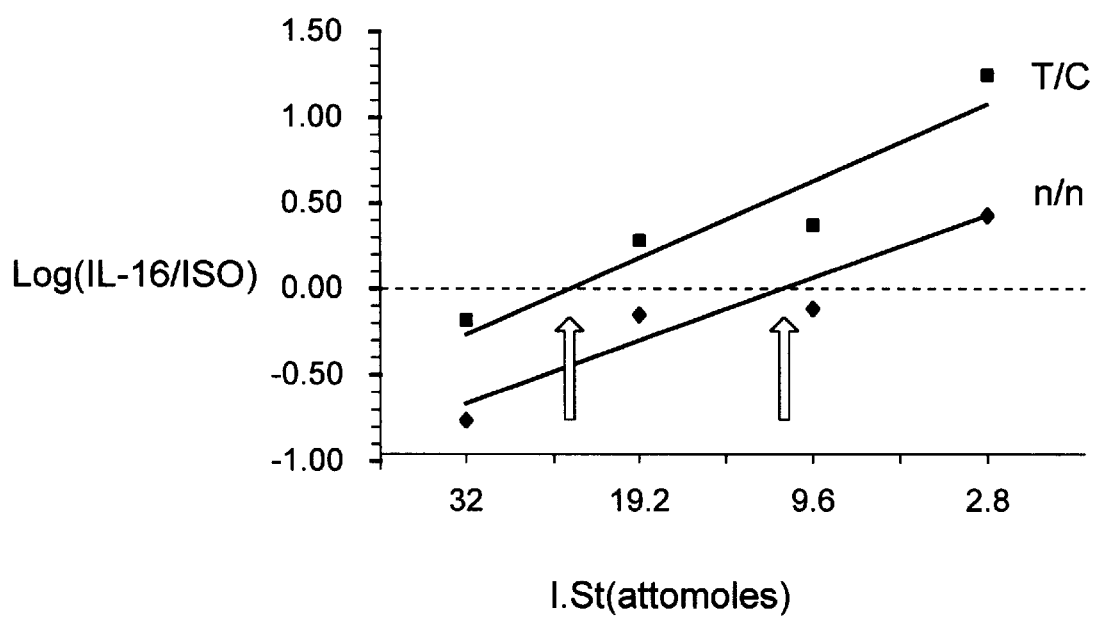
F I G. 2

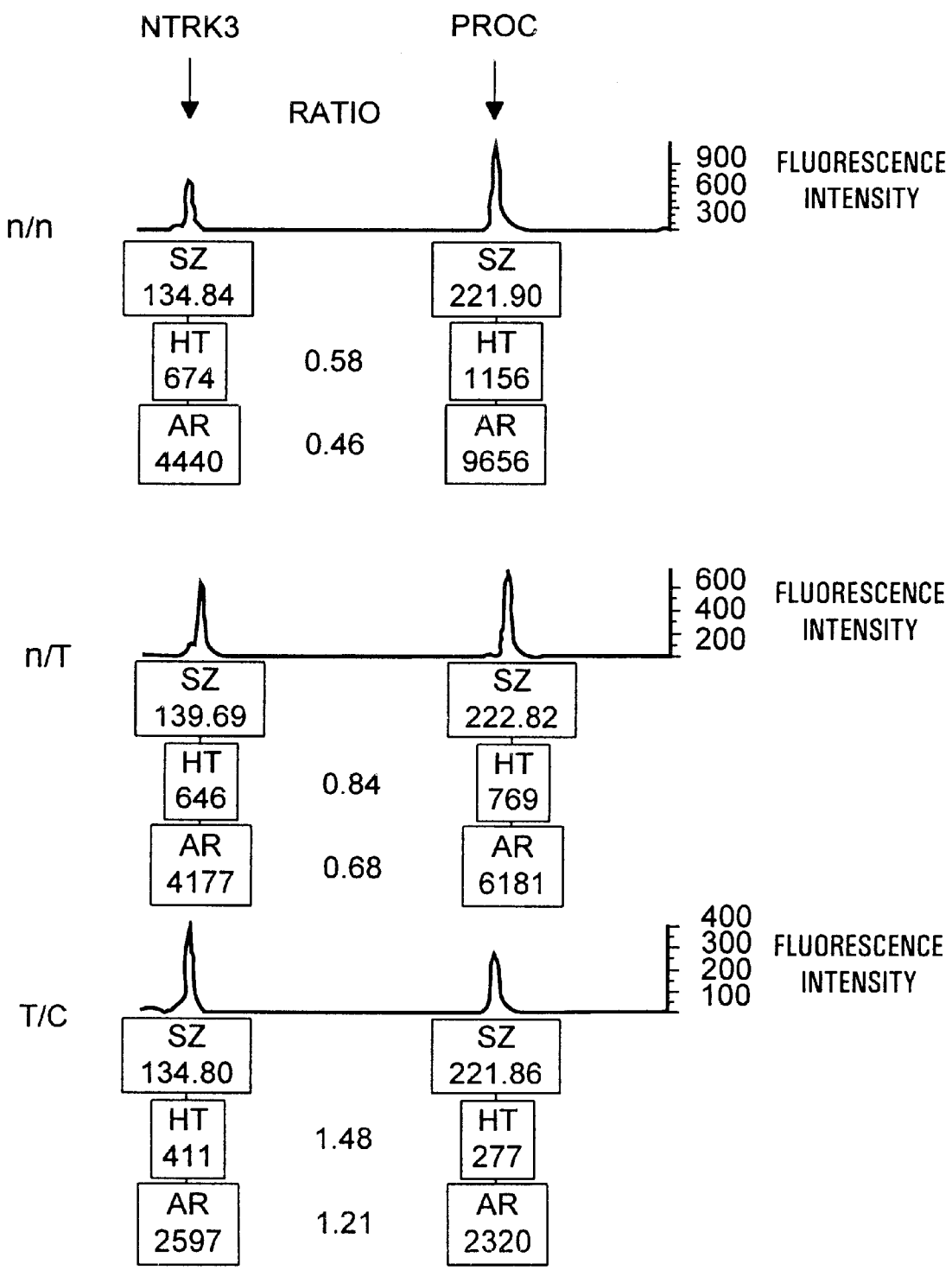
F I G. 6

DUPLICATIONS OF HUMAN CHROMOSOME 15Q24-25 AND ANXIETY DISORDERS, DIAGNOSTIC METHODS FOR THEIR DETECTION

FIELD OF THE INVENTION

Panic disorder, agoraphobia, social phobia and other anxiety disorders affect 5–10% of the general population. There are no biochemical, cytological or molecular tools for the diagnosis of anxiety disorders. Moreover, the gene or genes predisposing to anxiety disorders have not yet been localised. We have studied the clinical association between panic/agoraphobia and joint hypermobility syndrome, and have identified several pedigrees in which these disorders cosegregate. We have detected a 10 centiMorgan (cM) duplication of human chromosome 15 (15q24-25) in the affected subjects of families with several members suffering from anxiety and depression disorders. The 15q24-25 duplication segregates with panic disorder, agoraphobia, social phobia, depression and joint hypermobility syndrome. The 15q24-25 duplication is strongly linked to panic disorder, agoraphobia, social phobia and joint hypermobility syndrome (lod score 4.9). Affected-only analysis for the phenotype defined only by the anxiety disorders gave a lod score of 3.36. All but one of the 45 subjects of these families with these anxiety disorders had the 15q24-25 duplication. Mosaicism was detected in 80% of the affected subjects, with 40–70% of their lymphocytes having the 15q24-25 duplication. We have also studied 50 unrelated non-familial cases of panic disorder and/or agoraphobia and all had the 15q24-25 duplication. The duplicated region contains 10 known genes of which NTRK3 and LOXL1 are likely to be involved in anxiety and joint hypermobility. We propose that this genomic mutation, which is present in 7% of the general population, is the major susceptibility mutation for panic disorder, agoraphobia, major depression and social phobia in familial and sporadic cases. We have developed cytological, cytogenetic and molecular methods for the specific diagnosis of the 15q24-25 duplication causing anxiety disorders.

PRIOR ART

Anxiety disorders are neurotic alterations that include generalised anxiety disorder, phobic disorders, panic disorders (panic attacks, panic disorder and agoraphobia) and obsessive-compulsive disorders. The prevalence of this group of alterations is estimated in about 10% in the adult population and up to 5% in infantile patients. Several million people worldwide are affected by anxiety disorders, but the actual prevalence rates of these alterations are probably higher.

Anxiety and panic disorders aggregate in families. The familial transmission of anxiety disorders has often been explained by common familial environmental factors. Twin studies of anxiety disorders have shown a high concordance among monozygotic twins. The mode of familial transmission of panic disorder is unclear, but it has been suggested that anxiety, panic attacks and agoraphobia have an autosomal dominant pattern of inheritance with incomplete penetrance. Although a major gene is supposed to be involved in panic disorder, multifactorial/polygenic inheritance has also been postulated.

The search for the gene(s) involved in anxiety disorders has been focused in the study of candidate genes and wide genome analyses. So far, only a moderate association with a polymorphism of the serotonin transporter (5-HTT) gene has been found, and is estimate to account for 3–4% of the total genetic variation in anxiety[1]. The failure to detect linkage for panic disorder, after the analysis of a large number of families and markers under different models of inheritance with various degrees of penetrance and in spite of high informativity has been attributed to locus heterogeneity and complexity of the phenotypes.

A strong association between anxiety disorders and joint hypermobility has also been reported[6]. The link between joint hypermobility and anxiety disorders has been further been clarified by the identification of features of anxiety in about 70% of patients with joint hypermobility[3]. Joint hypermobility is about 17 times higher in patients with panic disorders than in control subjects. The investigation of these associations may lead to the identification of susceptibility mutations for anxiety disorders. We have identified and interstitial duplication of chromosome 15q24-25 in the patients affected by panic disorder, agoraphobia, social phobia, major depression and joint hypermobility of these families, and also in unrelated non-familial cases of panic disorder and agoraphobia. The 15q24-25 mutation is the major genetic alteration of susceptibility for these anxiety disorders.

NTRK3 as a candidate for anxiety disorders

Among the few known genes in the 15q24-25 duplicated region the best candidate for anxiety disorders is the gene that encodes the neurotrophin-3 receptor, NTRK3, (also known as TRKC)[6,7]. Although neurotrophic factors have potential importance in neurodegenerative diseases, they have other roles and it has been suggested that they participate in psychiatric disorders. Thus, neurotrophic factors are involved in plasticity of the nervous system and may mediate the changes in neural connections associated with learning and memory. Moreover, it has been observed that anti-depressant drugs cause modifications of the levels of expression of neurotrophins and their receptors, in particular neurotrophin-3 (NT-3).

Within the human adult CNS, NTRK3 is abundantly expressed in the noradrenergic neurons of the forebrain, including the cerebral cortex, hippocampus, thalamus and hypothalamus, and is the only neurotrophin receptor detected in the locus coeruleus (LC). The LC is the principal norepinephrine (NE) containing nucleus in the CNS, playing a major role in behavioural arousal in response to novel or stressful stimuli. A significant increase in central noradrenergic function is relevant for the pathogenesis of panic disorder because the NE system integrates and coordinates fear responses to threatening stimuli. The specific expression of NTRK3 in noradrenergic neurons and its location in the duplicated chromosomal region in patients with panic disorders, which might cause its over-expression, argues for NTRK3 as an excellent candidate for anxiety disorders. Thus, the over-expression of NTRK3 in the LC might induce an excessive trophic and proliferative effect on NE neurones. Indeed, stress and antidepressants regulate NT-3 expression in the LC. Since the major source of NE in the forebrain is the LC, the final consequence of the over-expression of NTRK3 would be an over-activity and enhanced efficacy of the NE synapses, resulting in a dysregulation of the NE response. This would decrease the emotional arousal threshold of the individual and alter the alarm/fear regulatory system.

We have clearly demonstrated by linkage and affected-only analyses that a chromosome 15q24-25 duplication is involved in familial cases of several anxiety disorders, confirming the heritable condition of these alterations and defining a common biological background for panic disorder, agoraphobia and social phobia. The fact that the duplication has also been detected in all the subjects of an independent sample of unrelated patients affected by panic disorder and/or agoraphobia, arises the view that this chromosomal alteration is the major susceptibility mutation for these anxiety phenotypes. Although the psychiatric-clinical spectrum of the dup15q24-25 mutation is still not completely defined, we have shown the co-occurrence of this mutation in several psychiatric clinical groups, panic with or without agoraphobia, social phobia and simple phobia. From this study, it is clear that a pure entity including panic and agoraphobia can not be maintained and that a panic-agoraphobic spectrum model or a general neurotic syndrome seems more realistic from the genetics point of view. The 15q24-25 duplicated region may contain more than 50 genes, of which only 10 have been precisely mapped. We have developed cytological, cytogenetic and molecular methods for the diagnosis of the 15q24-25 duplication. At present, NTRK3 and LOXL1 are good candidates to explain the anxiety disorders presented here and joint hypermobility syndrome. The development of transgenic mice that overexpress these genes might provide models for pharmacological and clinical studies of these dommon alterations.

Bibliography

1. Lesch, K. P., Bengel, D., Heil,s A., Sabol, S. Z., Greenberg, B. D., Petri, S., Benjamin, J., Muller, C. R., Hamer, D. H., Murphy, D. L. Association of anxiety-related traits with a polymorphism in the serotonin transporter gene regulatory region. *Science* 1996;274:1527–1530.

2. Bulbena, A., Duró, J. C., Mateo, A., Porta, M., Vallejo, J. Joint hypermobility syndrome and anxiety disorders. *Lancet* 1988;2:694.

3. Bulbena, A, Duró, J. C., Porta M, Martin-Santos R, Mateo A, Molina L. L. Anxiety disorders in the Joint hypermobility syndrome. *Psychiatr Res* 1993;46:59–68.

4. Nadal, M., Moreno, S., Pritchard, M., Preciado, M. A., Estivill, X., Ramos-Arroyo, M. A. Down syndrome: characterisation of a case with partial trisomy of chromosome 21 owing to a paternal balanced translocation (15;21) (q26;q22.1) by FISH. *J Med Genet* 1997;34:50–54.

5. Celi, F. S., Cohen, M. M., Antonorakis, S. E., Wetheimer, E., Roth, J., Shuldiner, A. R. Determination of gene dosage by quantitative adaptation of the polimerase chain reaction (gd-PCR): rapid detection of deletions and duplications of gene sequences. *Genomics* 1994;21:304–310.

6. Lamballe, F., Klein, R., Barbacid, M. TrkC, a new member of the trk family of tyrosine protein kinases, is a receptor for neurotrophin-3. *Cell* 1991;66:967–979.

7. Mcgregor, L. M., Baylin, S. B., Griffin, C. A., Hawkins, A. L., Nelkin, B. D. Molecular cloning of the cDNA for human TrkC (NTRK3), chromosomal assignment, and evidence for a splice variant. *Genomics* 1994;22:267–272.

8. Kim, Y., Boyd, C. D., Csiszar, K. A highly polymorphic (CA) repeat sequence in the human lysyl oxidase-like gene. *Clin Genet* 1997;51:131–132.

9. Cottingham, R. W., Idury, R. M., Schafer, A. A. Faster sequential genetic linkage computations. *Am J Hum Genet* 1993;53:252–263.

10. Ott, J. Analysis of human Genetic Linkage. $_2$nd ed. Baltimore, John Hopkins University Press, 1991.

11. Anastasis, J., LeBeau, M. M., Vardiman, J. W., Westbrook, C. A. Detection of numerical chromosomal abnormalities in neoplastic hematopoietic cells by in situ hybridization with a chromosome-specific probe. *Am J Pathol* 1990;136:131–139.

SUMMARY OF THE INVENTION

We have detected interstitial duplications of chromosome 15q24-25 in patients affected of panic disorders, depression and joint hypermobility in familial and apparently sporadic cases of panic disorders. The 15q24-25 duplication is present in 7% of the general population. This cytogenetic mutation is responsible :for the common and complex anxiety and mood disorders. The duplicated region contains at least 10 genes of which NTRK3 and LOXL1 are likely to be involved in anxiety and joint hypermobility, respectively. We have developed cytological and cytogenetic methods based on fluorescent in situ hybridization, for the detection of the 15q24-25 duplication and its associated somatic mosaicism. We have developed molecular methods, based on DNA or RNA analysis, for quantitative determination of genes (including NTRK3 and LOXL1) or other sequences from the 15q24-25 duplicate region. All these tests are used for the diagnosis of the anxiety and related disorders, including agoraphobia, social phobia, panic attacks, panic disorders, simple phobia, mood disorders, major depression and other associated pathologies.

DETAILED DESCRIPTION OF THE INVENTION

Co-segregation of panic and anxiety disorders, mood disorders and joint hypermobility Seven genealogies with several members affected of panic disorder and or agoraphobia were identified (Gratacós et al. in preparation). 19% of subjects had panic disorder and or agoraphobia, 22% social phobia, 34% simple phobia, and 18% major depression, according to the Structural Clinical Interview for DSM-III-R (American Psychiatric Association. Diagnostic and Statistical Manual of Mental Disorders (DSM-III-R). 3rd ed., revised. Washington D.C., The American Psychiatric Association; 1987). These frequencies are significantly higher than the prevalence of each of these disorders in the general population, indicating a common genetic basis and suggesting that these disorders might represent different clinical manifestations of the same underlying molecular alteration.

Joint hypermobility with Beighton scores[3] equal or higher than 4 were detected in 65 (44%) subjects of these families. Panic disorder and/or agoraphobia co-segregated with joint hypermobility syndrome in 64% of patients, social phobia in 59%, and simple phobia in 46%. Overall the co-segregation of any of these anxiety disorders with joint hypermobility syndrome was 54%.

Duplications of chromosome 15q24-25 in anxiety disorders

Co-segregation of anxiety disorders with joint hypermobility syndrome suggested the possibility of a continuous gene syndrome. We simultaneously started a segregation analysis with a set of microsatellite markers close to or within candidate genes for joint hypermobility syndrome (collagen, fibrillin, elastin, etc.) and a cytogenetic study, mainly focused on detecting any chromosomal rearrangement that may involve chromosomes that contain these candidate genes. In a sample of 16 affected subjects from the seven families a putative cytogenetic alteration on the long arm of chromosome 15 (15q24-25) was observed, which was subsequently identified as an interstitial duplication. Several YAC clones from this region were used to study the putative cytogenetic abnormality by fluorescence in situ hybridisation (FISH) . YACs 802-b-4, 929-c-7, 750-b-10, 891-e-7 and 753-h-11 clearly demonstrated an interstitial duplication at 15q24-25 (named dup15q24-25) in affected subjects (FIG. 1).

To determine the extent of the duplication, a YAC/PAC contig covering the 15q24-25 region was constructed (FIG. 2). A total of 41 YACs, 3 PACs and 2 BACs were used in the construction of the map. The information on the chimaerism and the STS content of the YAC clones has been deposited at CEPH. The duplicated region spans about 10 cM of human chromosome 15 between markers D15S739 (proximal) and D15S930 (distal). The region contains 10 known genes (LOXL1, CRABP1, IREB2, NIC3A, NIC5A, NIC4B, FAH, IL16, NMB, and NTRK3), which were localised to the duplicated region by PCR of their STSs. A large number of ESTs are known to be in the duplicated region, which might contain between 50 and 200 genes.

The centromeric limit of the duplication was located between YACs 753-h-11 and 875-a-3, which do not overlap (within the deleted YAC 33iF3), and the telomeric limit between YACs 802-b-4 and 966-a-2, which do not overlap either (within the deleted YAC 964-f-8). Several attempts were made to obtain YACs, PACs or BACs to cover these gaps. We obtained PACs 252-a-23 and 216-i-14 for the telomeric end, and PAC 251-c-23 for the centromeric end, but neither clone closed the gaps. However, since these PAC clones were located at the ends of the 15q24-25 duplication, we generated cosmid probes (t216-1 and c251-3) for FISH analyses of the duplication and segregation with the anxiety disorder phenotypes in the families.

The analysis of further samples from affected subjects of these families allowed the detection of three forms of the 15q24-25 duplication. The most common form was denominated "telomeric" and was found in 79% of the affected individuals. This telomeric duplication was observed as a direct (tandem) form or an inverted form, depending on the relative distance of the signals seen by FISH. Finally, a "centromeric" duplication, with the signals located far away from their original location and closer to the centromere, was detected in 21% of affected subjects of these families. These forms of the duplication are likely the result of different rearrangements of the same region at 15q24-25. Although the duplicated region and the markers in the centromeric and telomeric forms are the same, we can not exclude that additional centromeric or telomeric loci are involved in the duplications, or that a cluster of breakpoints exists in an interval of several kilobases.

To confirm that the duplication was a specific feature of the patients, 81 anonymous amniotic liquid samples from unrelated pregnancies were studied using probes t216-1 and c251-3, detecting the duplication in 5 samples (6.2%). Furthermore, 54 unrelated individuals, for whom panic and/or agoraphobia and joint hypermobility was not assessed, were also studied; we detected the 15q24-25 duplication in 5 of them (9.2%). Overall, from 135 unrelated control samples the telomeric and the centromeric duplications were found at frequencies of 70% and 20%, respectively.

Linkage between the 15q24-25 duplication and anxiety disorders

The strength of the relationship between the 15q24-25 duplication and several anxiety disorders and joint hypermobility syndrome was analysed in the seven families by linkage analysis. The anxiety phenotypes were studied under five models: 1) panic disorder and/or agoraphobia, 2) social phobia, 3) simple phobia, 4) panic disorder and/or agoraphobia and/or social phobia, and 5) same as 4 and/or simple phobia. These five models were also studied adding the joint hypermobility syndrome ($\geq$4 Beighton criteria), and this phenotype was also tested as a unique trait.

Table 1 shows the lod score values for linkage between the 15q24-25 duplication and the 11 models analysed under 78% and almost complete penetrance of the duplication. The highest lod score of 4.94, at a recombination fraction of 0, was obtained for the model that includes four traits (panic disorder and/or agoraphobia and/or social phobia and/or joint hypermobility syndrome). Significant linkage values were obtained for all the models that included joint hypermobility syndrome, with the exception of simple phobia with a lod score of 2.33. Joint hypermobility syndrome by itself gave a lod score of 3.82 at a recombination fraction of 0. None of the models with only psychiatric traits reached lod score values of 3, but the models with three or four anxiety phenotypes reached lod scores of 2.

The same 11 models were tested for affected-only analysis for the 15q24-25 duplication under these two levels of penetrance. A lod score of 3.36 was obtained for the phenotype defined by panic disorder and/or agoraphobia and/or social phobia and of 2.96 when the four anxiety phenotypes were considered. The addition of joint hypermobility syndrome to the model of panic disorder and/or agoraphobia and/or social phobia increased the led scores to 3.66. Lod scores of 3.1 and 3.28 were obtained for panic disorder and/or agoraphobia, and for social phobia, when joint hypermobility syndrome was also considered. Positive lod scores were also obtained for the other models but without reaching levels of significance (Table 1).

The phenotypic characteristics of 93 subjects of these seven families and their association with the 15q24-25 duplication are shown in Table 2. The proportion of duplicated subjects (72%) in these families is higher than in the general population (7%). Remarkably, all patients with social phobia had the duplication. Forty-four of the 45 patients (98%) with panic disorder and/or agoraphobia and/or social phobia had the 15q24-25 duplication. Similarly, 87% of subjects with joint hypermobility syndrome had the 15q24-25 duplication. When the clinical criteria was the co-existence of one or several psychiatric traits and joint hypermobility syndrome, all subjects had the duplication. Finally, among the patients with the duplication 53 (79%) had a diagnosis of one or several anxiety disorders, and among the non duplicated subjects only 1 (2%) had a diagnosis of panic disorder or/an agoraphobia (a patient with only agoraphobia). Among the members of the families without these anxiety disorders nor joint hypermobility syndrome 88% were negative for the dup15q24-25 mutation.

To replicate the study in a different group of patients we ascertained 50 unrelated patients with panic disorder and/or agoraphobia, who regularly attend an Anxiety Clinic from an area of Barcelona. Any possible relationship between the patients and those of the village was excluded. Remarkably, dup15q24-25 was detected in all 50 affected patients and in only 10 of 135 unrelated controls from the general population (Chi-square 138.5, with Yate's correction; P<0.0001, by Fisher's exact test; Odds ratio 1,207.2).

Several origins and mosaicism of the 15q24-25 duplication

The analysis of the families with 6 micro-satellite markers, four located within the 15q24-25 duplicated region (LOXL1, D15S154, D15S201 and NTRK3-BP2) and two outside the duplication (D15S1040 and D14S158), gave negative or less than 1 linkage values for all the phenotypic models tested in the families. These markers span a region of 20 cM on the genetic map of human chromosome 15 (the 4 markers within the duplication span about 10 cM). Interestingly, in the 67 subjects with the 15q24-25 duplication of these families we never detected 3 alleles, even when the duplication was present in three generations in the family. A total of 28 different haplotypes was generated with these 6 markers from a total of 71 duplicated chromosomes in which it was possible to unambiguously determine the mutated haplotype. In each family, the founder dup15q24-25 haplotypes were easily identified among the other haplotypes with the duplication carried by new members of the family. This high number of haplotypes (42% of the chromosomes with the duplication have different haplotypes) indicates independent origins and suggests that this mutation is easily generated. In at least 7 couples of these families both members carried the duplication. This represents 44% of the couples in which both members were analysed for the duplication and is a clear evidence of assortative matting for the phenotype(s) associated with the 15q24-25 mutation. There were several examples of abnormal segregation of the 15q24-25 duplication in the families, indicating the generation of a de novo case, the conversions from duplicated to non-duplicated chromosomes, and the conversion of one form of the duplication to the other.

Mosaicism for the 15q24-25 duplication was first observed by FISH in lymphocyte metaphase chromosomes when hybridised with probes t216-1 and c251-3. Mosaicism for dup15q24-25 was scored in 100 interphase nuclei of each individual, detecting a mediane of 55% duplicated cells (40.4–70.6%). The hybridisation efficiency of the probe in interphase nuclei in non-duplicated control subjects was 85%.

We have studied the 15q24-25 duplication in sperm from a non-duplicated control subject and in a patient homozygous for the duplication (15% homozygous for the duplication and 85% heterozygous). As expected, we only detected the duplication in the gametes of the affected individual, but only 40% of his spermatozoa had the duplication. Thus, this result demonstrates that the 15q24-25 duplication is present in germ cells and indicates that it is transmitted from one generation to another.

Cytologic detection of the 15q24-25 duplication in perypheral lymphocytes

Several DNA probes were used for the detection of the 15q24-25 duplication in perypheral lymphocyte preparations. Fluorescent in situ hybridisation (FISH) of interphase cells was performed as previously[4] described using probes t216-1 and c251-3, covering proximal and distal regions of the 15q24-25 duplication (FIG. 3).

Cytogenetic detection of the 15q24-25 duplication in peryperal lymphocytes

Several DNA probes were used for the detection of the 15q24-25 duplication in lymphocyte metaphase cells. FISH was performed as described previously[4] using probes t216-1 and c251-3.

Molecular detection of the 15q24-25 duplication in perypheral lymphocytes

Several genes or sequences from the 15q24-25 duplicated region were used for the molecular detection of the 15q24-25 mutation associated to anxiety disorders. The sequences described here are only examples of the sequences that can be analysed to detect the 15q24-25 duplication.

Quantitative RT-PCR RNA analysis of IL16

To assess the levels of expression of the genes contained in the 15q24-25 duplicated region, we selected IL16, which is sufficiently expressed in blood lymphocytes. Overexpression of IL16 was studied by quantitative PCR. As expected, the homozygous individual used against a control patient showed an approximately double concentration of cDNA in the peripheral blood lymphocytes (FIG. 2). The analysis of the expression of other genes in the region should exclude the possibility that the duplicated genes are silenced in patients with mutation dup15q24-25. Total RNA from cultured cell lines of affected and control individuals was amplified by competitive PCR[5]. The endogenous IL16 mRNA was amplified using primers corresponding to a 326 bp fragment (STS WI-7689) of the cDNA sequence of the gene (GenBank G06653) (forward primer: 5'-TCC CAT AAC CGC TGA TTC TC-3' and reverse primer: 5'-AAT AAA TGT CAC TGT TTG GGG G-3'). An internal standard was constructed with a 42 nucleotides primer in which 20 nucleotides at the 5' end correspond to 76 nucleotides upstream. Amplification with these primers results in a 228 bp product that was further subcloned in a pMOS Blue-T vector (Amersham) and used as internal standard. As the IL16 mRNA PCR product could be due to residual genomic DNA, control PCR amplifications of each sample were performed with previous treatment with RNAase A.

Quantitative Southern blotting analysis of the NTRK3 gene

Since the lysyl-oxidase like (LOXL1) and the neurotrophin 3 receptor (NTRK3) genes were located within the 15q24-25 duplicated region, were physically located at the opposite ends (FIG. 1), and were considered good candidates for the phenotypes observed in the patients, Southern blots were analysed with probes corresponding to these genes. Five $\mu$g of genomic DNA from affected and normal individuals was digested with 40 U of EcoRI (Boehringer-Mannheim) and the DNA was transferred to a nylon membrane (Hybond-N+, Amersham). With respect to normal subjects, dosage was expected to be 1.5 fold for the heterozygous patients and double for the patients homozygous for genes within the duplication, as compared to control genes located outside the duplicated region or on another chromosome. For this purpose, an EcoRI/SstI fragment of plasmid pNIJ3-SR0.4 containing a 5' cDNA portion of the NTRK3 gene (GenBank G913721), and a control marker from chromosome 2 (exon 7 of the rBAT gene) were labelled with $\alpha$ dATP$^{32}$P. Dosage was assessed on autoradiographs by quantitation of band density. FIG. 4b shows the comparative analysis of the NTRK3 gene with the rBAT gene, on chromosome 2. Quantitation of band density, peak height and comparison with the control marker clearly indicated increased band intensity in the individuals carrying the duplication.

Quantitative PCR DNA analysis of NTRK3

Since the neurotrophin 3 receptor (NTRK3) gene was located within the 15q24-25 duplicated region and was considered a good candidate for the anxiety phenotype, dosage analysis was assessed through simultaneous PCR amplification of two fragments, one corresponding to a NTRK3 gene fragment and the other one to a control fragment of PROC gene (exon 1). Primers corresponding to a 134 bp fragment NTRK3 gene were: TRK3U2, fluorecently labelled at 5' end: 5'-TAT GAA GAT GTT CGC TTC AG-3' and TRK3U2F 5'-TCT ACC TGG ACA TTC TTG GCT-3'. Primers corresponding to a 222 bp fragment of PROC gene were: PC111, fluorecently labelled at 5' end: 5'-GTG CTA GTG CCA CTG TTT GT-3' and PC112 5'-ATC ACC ACC TAG CTC TCT TC-3'. Samples were run in an ABI PRISM 373 DNA sequencer and the results were processed by GENESCAN and GENOTYPERä softwares. A PCR co-amplification of a fragment of NTRK3 and a control fragment of the PROC gene showed dosage differences due to the 15q24-25 duplication (FIG. 4).

Southern and PCR analysis were only useful when the rate of the duplicated cells in blood lymphocytes of the individual (assessed by scoring the percentage of duplicated vs. normal in interphase nuclei by FISH) was high enough to give a definite and reproducible difference between peaks. In fact, the presence of mosaicism complicated considerably the evaluation of the duplication by either Southern or PCR.

Methodology used in the implementation of the invention

Clinical evaluation of patients

All patients were evaluated for panic disorder with or without agoraphobia, social phobia, simple phobia, and major depression, according to the Structural Clinical Interview for DSM-III-R.

Cytogenetic and fluorescent in situ hybridisation analysis

Metaphase chromosome spreads were prepared after harvesting 72 h amniocyte cultures and lymphocyte cultures from peripheral blood of the patients according to standard methods. GTL banding techniques were performed in all cases. Peripheral blood cultures were synchronised with methotrexate to obtain high resolution chromosomes at a level of 900 G bands. Non stained slides were kept at −20° C. until hybridisation. Prior to hybridisation, slides were baked at 55° C. for 30 min. Slides were mounted with 40 µl of antifade solution (Vector Laboratories) containing 0.5 mg/ml of propidium iodide or 150 ng/ml of DAPI.

We generated probes from YAC, BAC and PAC clones by inter Alu-PCR using primers A33 and A44 as described[4]. The PCR products were ethanol precipitated and re-suspended in 40 µl of distilled water before labelling. All the probes used for FISH (cDNAs, cosmids, YACs and PACs) (2 mg of each probe) were labelled with either biotin-16dUTP or digoxigenin-11dUTP (Boehringer-Mannheim) by a standard nick translation reaction and then were gel filtrated. 400 ng of each probe were then ethanol precipitated with 1 mg of cot1-DNA (GIBCO-BRL) and 1 mg of salmon sperm DNA (Sigma) and re-suspended in a hybridisation mix containing 50% formamide and 50% of 12×SSC and dextran sulphate.

FISH was performed as described elsewhere[4]. Briefly, 70 ng of each probe (7 ml of the hybridisation mix) were applied to each slide and sealed with rubber cement (when hybridising more than one probe at a time, 5 ml of each probe were applied instead). After heat denaturation of the slides at 80° C. for 8 min, they were indubated overnight at 37° C. in a humid chamber. Post hybridisation washes were performed in three changes of 50% formamide and 50% 2×SSC followed by three changes of 2×SSC all at 42° C. Then slides were incubated in blocking solution (Boehringer Mannheim) for 10 min. Detection was performed by incubating the slides with either avidin-FITC (for probes labelled with biotin) or with anti-digoxigenin-TRITC (for probes labelled with digoxigenin) (both antibodies from Vector Laboratories) for 20 min at 37° C. in a humid chamber and then washed in two changes of 4×SSC/0.1% Tween-20. For cDNA probes and for cosmid probes, biotin signals were amplified once by incubating the slides with biotinylated anti-Avidin (Vector Laboratories) for 20 min, washed as mentioned above and the incubated again with Avidin-FITC for another 20 minutes and washed again. Slides were mounted with an antifade solution (Vectashield, Vector Laboratories) containing 0.1 mg/ml of DAPI. Slides were studied under a fluorescence microscope (VANOX, Olympus) equipped with the appropriate filter set. Images were analysed with the Cytovision system (Applied Imaging Ltd., UK). For each hybridisation, at least 20 metaphases were studied.

Interphase nuclei analysis

The detection of mosaicism by FISH was made taking into account the technique efficiency in known diploid controls. Patients were considered duplicated when the percentage of nuclei displaying three hybridisation signals exceeded two standard deviations the mean of false trisomic signals in control samples (30%)[11]. One hundred nuclei were analyzed in each control and test sample.

FISH in sperm

Collected sperm was first washed three times in PBS. Two drops of the suspension were then dropped on a clean slide and air dried. Slides were kept at −20° C. until FISH analysis. Prior to the hybridisation, the sperm heads were decondensed by rinsing the slides in 2×SSC for 3 minutes, dehydrated through an ethanol series (70, 80, 95%) and incubated for a maximum of 10 minutes in DTT 5 mM at 37° C. Slides were then rinsed another 3 minutes in 2×SSC and dehydrated again in an ethanol series. FISH was performed as described previously.

Southern analysis and PCR-DNA dose assessment

High molecular weight DNA was isolated from peripheral blood by salt precipitation. Five mg of genomic DNA from affected and normal individuals was digested with 40 U of EcoRI (Boehringer-Mannheim) following the manufacturer's instructions and electrophoresed in a 1% agarose gel in 0.5× TBE buffer for 12 hr. DNA was transferred in SSC 20× to a nylon membrane (Hybond-N+, Amersham). An EcoRI/SstI fragment of plasmid pNIJ3-SR0.4 containing 400 bp of the 5' cDNA of NTRK3 (GenBank G913721) and a control marker from chromosome 2 (rBAT gene fragment) (GenBank G349705) were labelled with $\alpha$ dATP$^{32}$P to high specific activity ($5\times10^{-9}$ cpm) by the random hexamer primer method. Hybridisations were carried out overnight at 65° C. and washed to a stringency of 0.1× SSC, 0.1% SDS for 15 min. Filters were placed against X-ray film (Curix, Agfa) overnight at −80° C. Dosage was assessed on autoradiographs using a densitometer (Phoretix) by quantitation of band density, pick height and comparison with the control marker within each lane.

Alternatively, dosage analysis was assessed trough PCR amplification of two fragments in the same reaction tube, one corresponding to a 3' cDNA fragment of the NTRK3 gene (GenBank G913721) and the other to a control fragment (exon 1) of PROC gene. PCR reactions were carried out in a 10 ml volume containing 10 ng of genomic DNA, 0.2 mM dNTPs, 1.5 mM MgCl$_2$ PCR buffer, 0.1 U of Taq Polymerase (Boehringer Mannheim) and 0.8 µM of NTRK3 primer pair and 1.2 µM of PROC primer pair. PCR conditions were, 94° C. for 3 min to denature followed by 22 cycles of 94° C. for 30 sec, 56° C. for 50 sec, and 74° C. for 30 sec. Samples were mixed with loading buffer, denatured at 94° C. for 5 min and run in an ABI PRISM 373 DNA sequencer (Perkin-Elmer). The results were processed by GENESCAN software and allele assignation, as well as its area and pick height, were carried out by use of GENO-TYPERa software.

mRNA dosage analysis in cultured cell lines

Total RNA from cultured cell lines of affected and control individuals was prepared using the guanidium chloride method and cesium chloride gradient. Competitive PCR was according to Celi[5]. RT-PCR was attempted with 5 µg of total RNA with Superscript and random primers (Gibco, BRL). Co-amplification of target and internal standard was performed as follows: 1 µl of RT product was included in a mixture containing 0.2 mM dNTPs, 1.5 mM MgCl$_2$ PCR buffer, 0.1 U of Taq Polymerase and 0.5 µM target sequence primer pair and 1 µl of varying amounts of internal standard. PCR conditions were as follows: 94° C. for. 4 min to denature followed by 30 cycles of 94° C. for 30 secs, 56° C. for 30 sec, and 74° C. for 30 sec.

Map construction

Based in the Whitehead Institute for Biomedical Research/MIT Center for Genome Research contig of YACs and STS content of chromosome 15 (http://www-genome.wi.mit.edu /cgi-bin/contig/phys_map), we narrowed the limits of the 15q24-25 duplication). YACs were obtained from Fondation Jean Dausset-CEPH (www.cephb.fr) and clones were confirmed to map to chromosome 15q24-25 using FISH analysis and further refined by PCR amplification of STSs content. The CEPH human ("mega") YAC was also screened by PCR amplification of a fragment of the LOXL1 gene but no positive clones were obtained. The ICI humanYAC library (filters maintained and distributed by HGMP-Resource Center, UK, www.hgmp.mrc.ac.uk.) was screened using primers of exon 7 of LOXL1 gene (Gen Bank G307145) as a probe and we found a positive YAC containing LOXL1 (33i-F3).

We used different kinds of probes to screen the human PAC library filters from HGMP-Resource Center (UK) (www.hgmp.mrc.ac.uk) and the human BAC library filters from Research Genetics, Inc. (Huntsville, USA) to fill the gaps and extend the contig and exactly define the limits of the duplication. A total of 57 STSs were used to position the PAC, BAC and YAC clones. The primers were acquired from Genset (France) or alternatively synthesised using an 392 DNA/RNA synthesiser (Applied Biosystems).

PCR amplifications were carried out in 25 µl reactions with 100 ng of template DNA, 0.5 µM of each oligonucleotide primer, 0.2 mM dNTPs, 1.5 mM $MgCl_2$ PCR buffer and 0.1 U of Taq Polymerase. Each reaction was denatured for 5 min at 94° C., followed by 35 cycles of 30 sec at 94° C., 30 sec at 50–65° C. (depending on the primer) and 4 sec at 74° C., as well as a final 5 min extension at 72° C.

The localisation of previously cloned and positioned genes to the duplicated region was performed by PCR amplification of the STSs known to contain fragments of the genes. Alternatively, and for those genes supposed to be located within the region by either linkage, hybrid somatic or cytogenetic studies, primers corresponding to the 3' region of their cDNA were synthetised and the genes located by PCR amplification from the YACs covering the zone.

Detection of Polymorphic Markers for Genotype Determination

To study the segregation pattern in the families different 15 q microsatellite markers were amplified: a dinucleotide repeat contained in intron 1 of the LOXL1 gene[8], D15S154, D15S201, D15S158, D15S140 and NTRK3-BP2, a newly described microsatellite identified from the sequence of a 1.5 kb BamHI single-copy subclone of PAC 252 A23 (isolated from the human PAC library of HGMP-Resource Center (UK) using the 3' end probe of the NTRK3 gene). The repeat sequence is $(CA)_{24}$ and the primers used to amplify this marker were: BP2F 5'-TTG CTT GAA GGG CAC CTG-3' and BP2R 5'-AAC ATC CTG GGT ACA TGC-3'.

For PCR amplification, in the case of LOXL1, D15S154, D15S201 and D15S158 the GT strand oligonucleotide primer flanking the (GT)n sequence was end-labelled with polynucleotide kinase (USB). PCR was performed using standard conditions in a 25 µl reaction volume in a mixture containing 100 ng of genomic DNA, 1 µM each oligonucleotide primer, 0.2 mM dNTPs, 1.5 mM $MgCl_2$ PCR buffer and 0.1 U of Taq Polymerase. The amplification conditions consisted of an initial denaturation step of 5 min at 94° C., followed by 30 cycles of 30 sec at 94° C., 30 sec at 58–65° C. (depending on the primer) and 40 sec at 74° C., as well as a final 5 min extension at 72° C. Reaction products (2 µl) were mixed with 2 µl of formamide stop solution and electrophoresed in a 6% polyacrylamide DNA sequencing gel at 40 W for 3.5 to 4 hours. Gels were dried and autoradiographed for 4–12 hours by exposure to X-ray film (Curix, Agfa) at −80° C. Markers D15S822, D15S1040 and NTRK3-BP2 were amplified following the same above reaction conditions but reverse primers were not end labelled. Instead, 2 µl of reaction products were mixed with 2 µl formamide stop solution and electrophoresed in a 5% polyacrylamide DNA sequencing gel at 40 W for 4–5 hours. Gels were silver stained and dried.

Linkage and association studies

For the psychiatric and joint hypermobility syndrome traits an autosomal pattern of inheritance with incomplete penetrance was considered. The final penetrance values (P) for the different genotypes of the locus trait allows for psychiatric diagnosis errors (c), in terms of: P=f c+(1−f)(1−c); being f the penetrance for a given genotype and c the probability of a correct diagnosis (affected versus non-affected), according to Ott (Ott, 1991). Thus the penetrances were: P=0.05 for genotype +/+, allowing both for phenocopies or diagnosis errors; P=0.736 for genotype +/D and P=0.9 for D/D; being + the wild type allele and D the deleterious allele.

The 15q24-25 duplication was entered in the analysis as an affection status or dichotomous locus type. To allow the inclusion of all the observed traits of this cytogenetic phenomena, we considered the genotype inherited from the respective parent and present in the zygote as the true genotype, which is DUP/DUP, DUP/+ or +/+; being DUP the "deleterious duplicated allele" carrying the 15q24-25 mutation and + the non duplicated wild type allele. The observed phenotype originates from this zygote genotype, which is observed by FISH and includes mosaicism. The penetrance values for this locus trait are the probabilities to observe by FISH a final phenotype given the zygote original genotype. Additionally, we have also considered the possibility of cytogenetic diagnostic errors (c) due to probe efficiency or missinterpretation. In this way we considered 3 liability classes (LC): LC1 was built for the unaffected or non-duplicated cases, coded as "1 1" in the linkage pedigree standard format (for affection status and liability class, respectively). The penetrances (1−P) for LC1 were 0.9 (+/+), 0.05 (+/DUP) and 0.01 (DUP/DUP). LC2 was built for "duplicated in heterozygosis", entered as "2 2" in the linkage pedigree format. The LC2 penetrances (P) were 0.05 (+/+), 0.90 (+/DUP) and 0.05 (DUP/DUP). LC3 was built for "duplicated in homozygosis" cases, entered as "2 3" and with the following penetrances (P): 0.01 (+/+), 0.05 (+/DUP) and 0.90 (DUP/DUP). We also considered an "almost complete penetrance" model with penetrances for LC1 (1−P): 0.99 (+/+), 0.01 (+/DUP) and 0.001 (DUP/DUP); for LC2 (P): 0.001 (+/+), 0.99 (+/DUP) and 0.01 (DUP/DUP); for LC3 (P): 0.001 (+/+), 0.01 (+/DUP) and 0.99 (DUP/DUP). We assumed the same values of disease or wild type allele frequencies (q) for both trait loci (D or DUP), and they were calculated according to the incidence of the psychiatric phenotype or the detection of the duplication in the general population, which gave similar values (see results): q≅0.075. This has a little influence in our analysis, because most members of the pedigrees were diagnosed (typed) and it was thus possible to infer their genotypes in thi;s way.

We have performed two point linkage analysis between the two loci traits using the function MLINK from the FASTLINK V2.2 software package[9]. We have entered the data files according to the above mentioned considerations. We tested the 11 models of psychiatric/joint hypermobility syndrome phenotypes, as indicated in the results section. We have also performed an affected-only test[10] for the 11 models to investigate the influence of the penetrance and diagnostic criteria.

We also considered four markers located within the 15q24-25 duplicated region (LOXL1, D15S154, D15S201 and NTRK3-BP2) and two outside the duplication (D15S1040 and D14S158). The map position and genetic distances between markers have been described (http:// www.cephb.fr). For the analysis we considered equal allele frequencies for each marker loci. We have performed two point calculations between the above mentioned markers and the loci trait. Additionally we have recalculated the genetic distances between markers. In this way we can also search for recombination differences due to the influence of the 15q24-25 duplication.

Explanation of the figures

Identification and characterisation by FISH of the 15q24-25 duplication with YAC and cosmid probes in patients with panic disorder and joint hypermobility syndrome. a/ Comparison of the G-banding pattern and the FISH analysis (using YAC 750-b-10) of both chromosomes 15 homologues of a subject with the interstitial duplication 15q24-25. The ideograms of chromosomes 15 show the normal pattern and the one generated by the interstitial duplication. Note that the duplicated chromosome shows a double hybridisation signal at 15q24-25 and that it appears considerably longer when compared to its normal homologue. b/ FISH analysis of both chromosome 15 homologues of a patient with panic disorder and the telomeric direct type of duplication using cosmids c251-3 and t216-1. In both experiments a control probe from chromosomal region 21q22.1 (YAC 230e8) was used (in red) to assess the condensation of the chromatin in each metaphase. c/ Chromosome 15 homologues of a patient with panic disorder and the telomeric inverted type of dup15q24-25 in homozygosity. FISH with cosmids t216-1 (in green) and c251-3 (in red) clearly shows that both homologous chromosomes 15 carry the same type of duplication. The two red signals are far apart, while a single green signal is detected. d/ Chromosome 15 homologues of a patient with panic disorder and the centromeric direct type of dup15q24-25. FISH with cosmids t216-1 (in green) and c251-3 (in red) shows the interstitial duplication of both probes in a quite more centromeric region of chromosome 15, while the normal chromosome 15 shows the normal pattern of hybridisation of both probes.

Figure 1A:
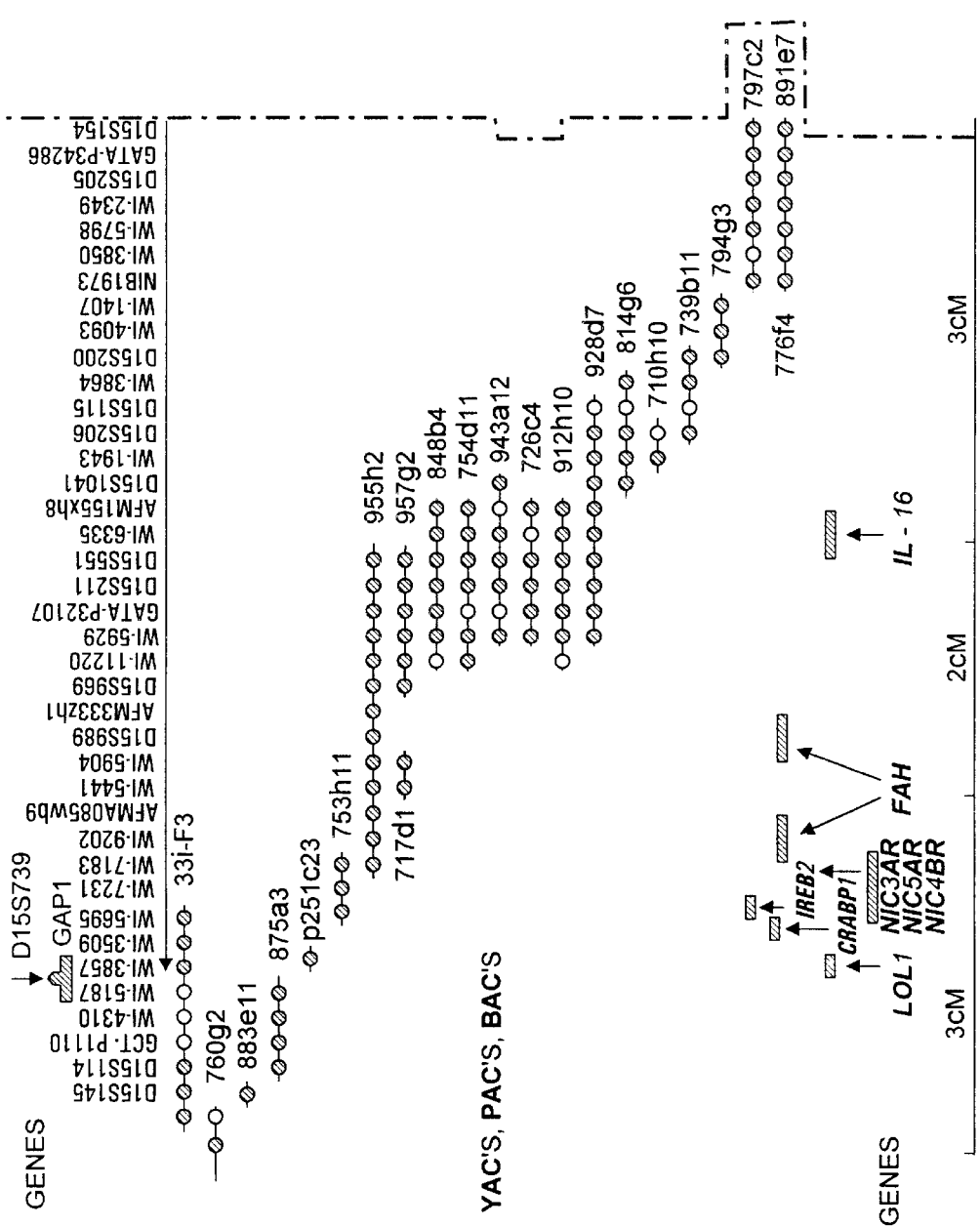
FIG. 1
Figure 1B:
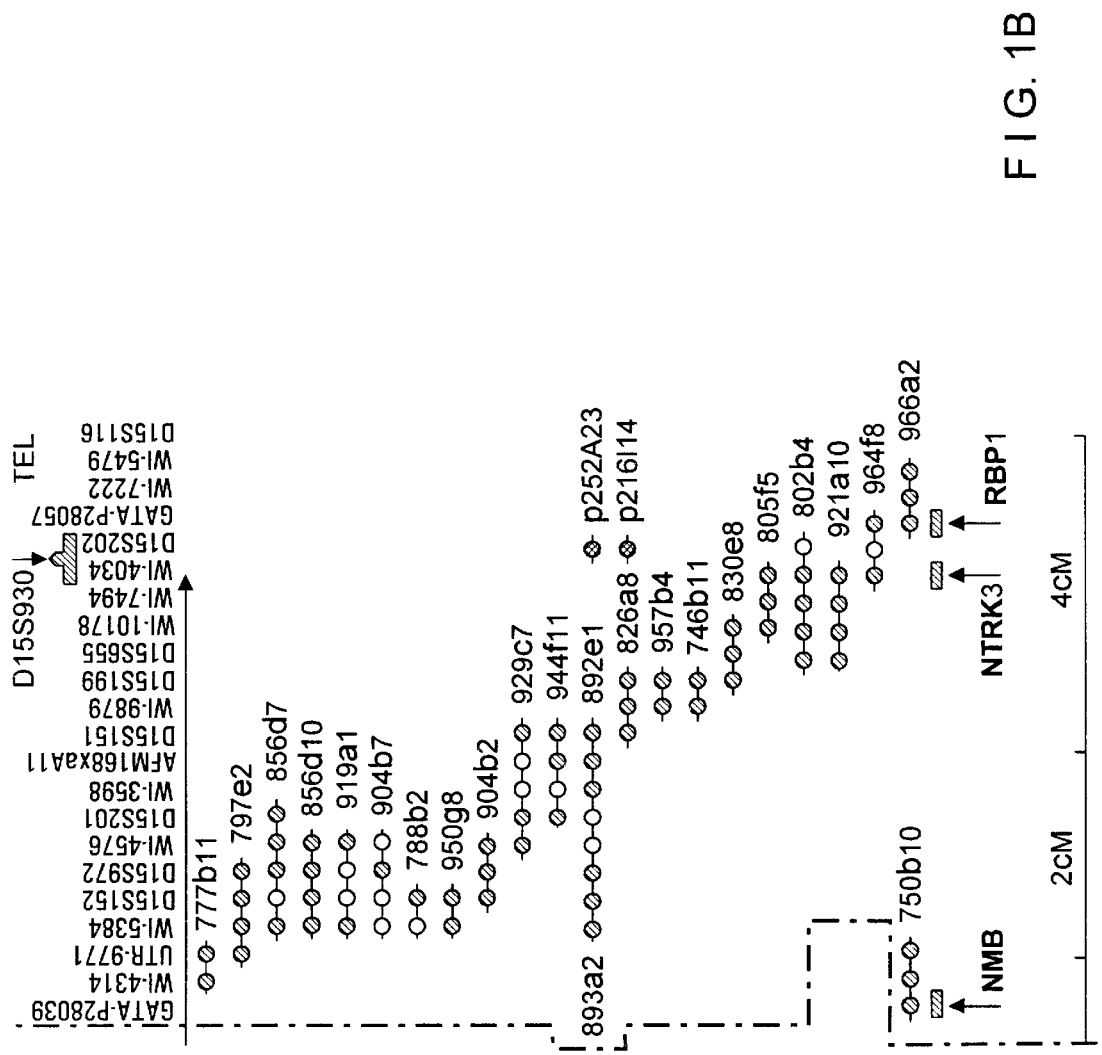
Figure 3:
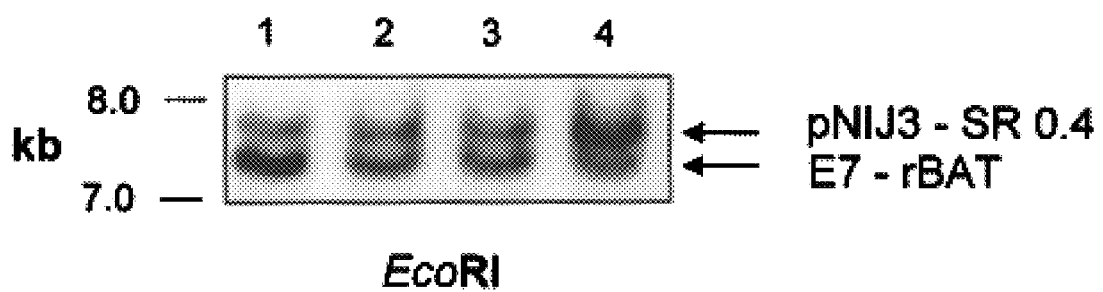
Figure 5:
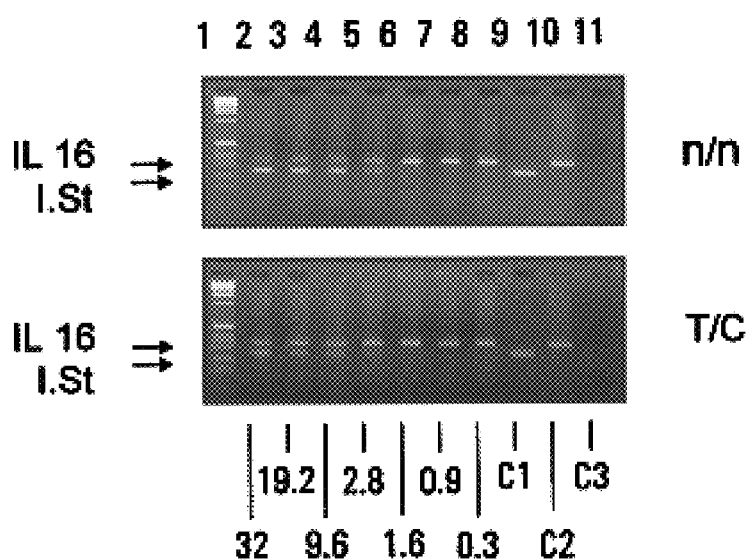
Figure 4:
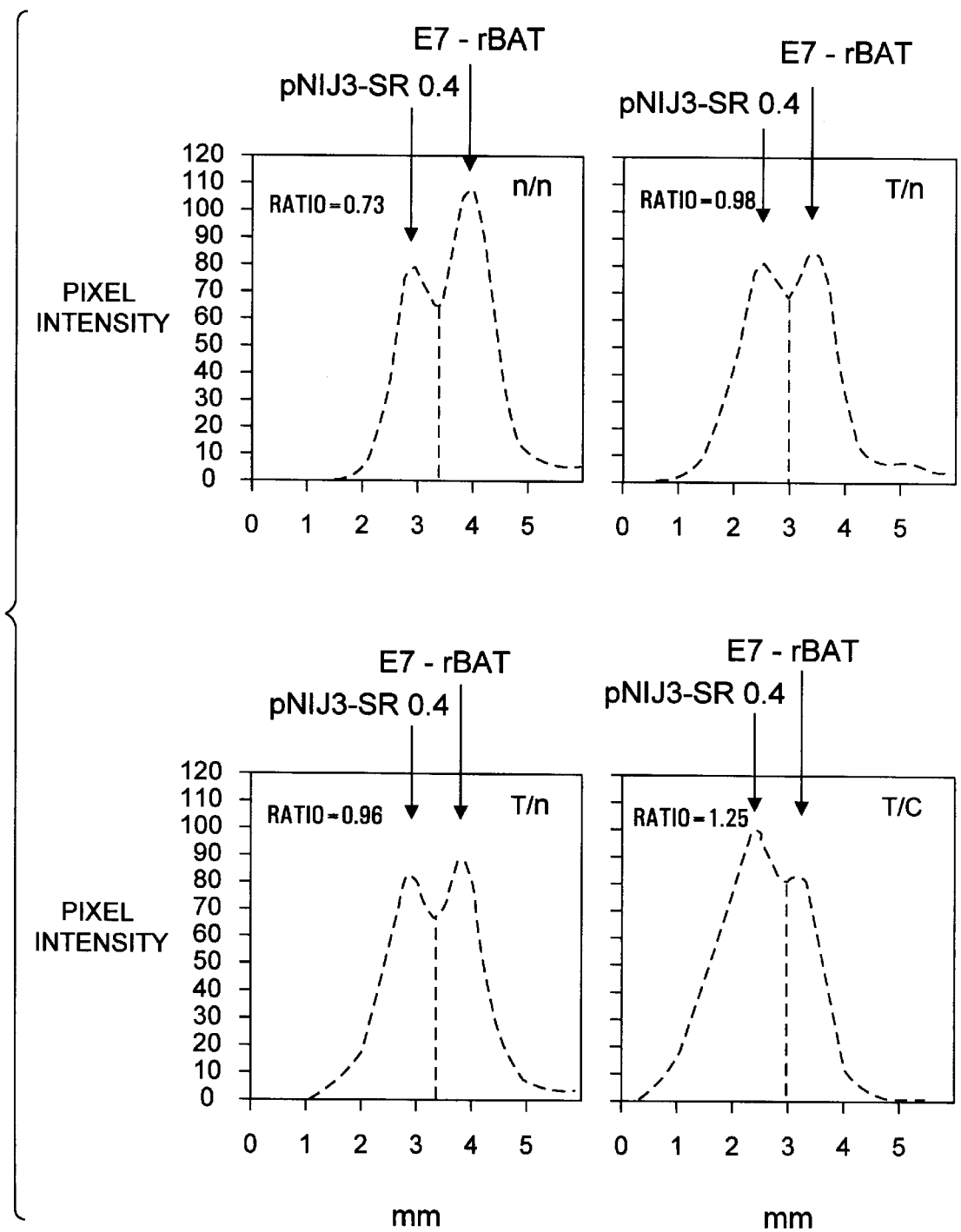

Physical map of the 15q24-25 region, which is duplicated in patients with anxiety and joint hypermobility disorders. The order of markers is based on available information (http://www-genome.wi.mit.edu/cgi-bin/contig/phys_map) and the locations have been tested for each marker and clone. The 57 STSs spanning the region are noted above a horizontal bar, that represents this region of the chromosome, with the arrows heads indicating its centromeric (CEN) and telomeric (TEL) ends. The markers are spaced at equal intervals. Genetic distances below the map are based on data from the same source. All the YAC clones are from CEPH, with the exception of YAC 33iF3, which is from ICI. The horizontal PAC and BAC numbers are preceded by P or B, respectively. The solid circles in the YACs, PACs and BACs represent STSs contained in the clone, and the open circles STSs that are absent in the clone. Vertical arrows and filled horizontal bars indicate the location of genes within YAC, PAC or BAC clones. Only RBP1 maps outside the 15q24-25 region.

FISH analysis in the interphase nuclei of lymphocytes and sperm of patients with panic disorder and joint hypermobility syndrome. a/ Two interphase nuclei (G1 state) of a patient with the 15q24-25 in heterozygosity hybridised with cosmid t216-1 (in green) and a control cosmid of chromosomal region 21q22.1 (in red). b/ Two interphase nuclei of an heterozygous patient for dup15q24-25 hybridised with cosmid t216-1 indicating mosaicism (100 cells were examined). c/ An interphase nucleus in G2 of a homozygous patient for dup15q24-25 hybridised with cosmid t216-1 showing the four FISH double signals. d/ Interphase nucleus in G2 state of a heterozygous patient for the 15q24-25 duplication hybridised with cosmid c251-3. e and f/ FISH analysis of the interstitial duplication of chromosome 15q24-25 in the sperm of a patient with panic disorder and joint hypermobility syndrome. e/ Hybridisation with probes c251-3 (in red) and t216-1 (in green) showing how two of the spermatozoa are normal while a third one carries the 15q24-25 duplication. f/ Hybridisation with probes t216-1 (in green) and a control probe from 21q22.1 (in red) on a spermatozoa of the same patient. In the same sperm head cosmid t216-1 appears clearly duplicated while the control probe only shows one hybridisation signal.

FIGS. 2–4

Dosage analyses for genes located within the 15q24-25 region in subjects with anxiety disorders and joint hypermobility syndrome. a/ Determination of the 15q24-25 duplicated region for the NTRK3 gene by Southern blot analysis of EcoRI-digested genomic DNA from a normal control (lane 1), two 15q24-25 heterozygous patients (lanes 2 and 3), and an homozygous patient (lane 4) with probe pNIJ3-SR0.4 (NTRK3) and the control probe E7-rBAT (rBAT). The 15q24-25 duplication was assessed by FISH in all the samples. The relative intensities of the peaks for each probe are indicated by the vertical arrows. Ratio values for heterozygous patients are higher than the ones for control samples. The homozygous patient has higher peak ratio values than heterozygous individuals (1.3 fold) and the control subject (about 1.7 fold). The genotypes are n/n for the normal subject, T/n for the heterozygous for the telomeric duplication, and T/C for a compound heterozygous for the telomeric and centromeric duplications.

FIG. 5

Chromatograms of the quantitative fluorescent PCR analysis of the NTRK3 and PROC genes of a control individual (n/n) and duplicated patients (T/n and T/C). The sequencer traces and the calculated ratios for height and area are shown. The height ratio was 1.4 fold higher for a heterozygous (T/n) subject and 2.5 fold for a homozygous (T/C) subject vs. a normal control (n/n).

FIG. 6

Quantitation of the human IL16 mRNA expression in cultured cell lines from a patient homozygous for dup15q24-25 and from a normal subject. Ethidium bromide staining of PCR products separated on a 1.5% agarose gel. The upper band corresponds to the target cDNA (IL16) and the lower fragment to varying dilutions of the internal standard (I.St.), which are 32, 19.2, 9.6, 2.8, 1.6, 0.9 and 0.3 attomoles, for lanes 1 to 8, respectively. Lanes 9 to 11 correspond to the I.St., IL16 and blank controls, respectively. The equivalence point for a 1:1 ratio between IL16 and I.St. in the control individual corresponds to dilution 3 (9.6 attomoles); while in the homozygous patient the equivalence point lies between lane 1 (32 attomoles) and lane 2 (19.2 attomoles). The DNA intensity of bands after RT-PCR were quantitated; the logarithm of the ratio of integrated optical density of IL16 vs the I.St. was plotted against the amount of total I.St. (attomoles) included in the PCR reaction. Vertical arrows indicate the equivalence point (ratio 1:1 or $\log_{10} 1=0$) of each sample. The genotypes n/n and T/C, correspond to normal and compound heterozygous for the centromeric and telomeric 15q24-25 duplications.

TABLE 1

Pairwise and affecteds-only lod scores for linkage of anxiety disorders (panic disorder, agoraphobia, social phobia and simple phobia) and joint hypermobility syndrome to the 15q24-25 duplication

| Phenotype | Pairwise | | Affecteds-only | |
|---|---|---|---|---|
| | Partial Pen. | Full Pen. | Partial Pen. | Full Pen. |
| PD ± A (± JHS) | −0.50 (4.29) | −0.58 (4.28) | 1.63 (3.10) | 1.84 (3.16) |
| SoPh (± JHS) | 0.02 (4.16) | −0.09 (3.92) | 2.00 (3.28) | 2.36 (3.28) |
| SiPh (± JHS) | −0.28 (2.33) | −0.59 (2.01) | 1.37 (2.63) | 1.40 (2.42) |
| PD ± A ± SoPh (± JHS) | 2.04 (4.94) | 1.83 (5.00) | 3.36 (3.66) | 3.71 (3.66) |
| PD ± A ± SoPh ± SiPh (± JHS) | 1.89 (3.33) | 1.45 (3.16) | 2.96 (2.88) | 2.92 (2.64) |
| JHS | 3.82 | 3.79 | 2.78 | 2.88 |

The phenotypes were panic disorder (PD), agoraphobia (A), social phobia (SoPh), simple phobia (SiPh) and joint hypermobility syndrome (JHS); All values are $Z_{max}$ at $\theta = 0$

TABLE 2

Distribution of phenotypes for anxiety disorders and joint hypermobility syndrome in patients from seven pedigrees

| | 15q24-25 mutation | | |
|---|---|---|---|
| Phenotype | DUP (%) | non-DUP (%) | Total |
| PD ± A | 25 (96) | 1 (4) | 26 |
| PD ± A ± JHS | 50 (88) | 7 (12) | 57 |
| SoPh | 27 (100) | 0 (0) | 27 |
| SoPh ± JHS | 54 (90) | 6 (10) | 60 |
| SiPh | 32 (86) | 5 (14) | 37 |
| SiPh ± JHS | 57 (84) | 11 (16) | 68 |
| JHS | 42 (87) | 6 (13) | 48 |
| PD ± A ± SoPh | 44 (98) | 1 (2) | 45 |
| PD ± A ± SoPh ± JHS | 59 (91) | 7 (9) | 65 |
| PD ± A ± SoPh ± SiPh | 53 (90) | 6 (10) | 59 |
| PD ± A ± SoPh ± SiPh ± JHS | 63 (84) | 12 (16) | 75 |
| No anxiety disorder | 13 (39) | 20 (61) | 33 |
| No JHS | 27 (57.4) | 20 (42.6) | 47 |
| Neither anxiety disorder nor JHS | 6 (12) | 14 (88) | 20 |
| Individuals tested for dup 15q24-25 | 67 (72) | 26 (28) | 93 |

The phenotypes studied were panic disorder (PD), agoraphobia (A), social phobia (SoPh), simple phobia (SiPh) and joint hypermobility syndrome (JHS); DUP, dup15q24-25.

What is claimed is:

1. A method for identifying a person at risk for developing an anxiety disorder, said anxiety disorder selected from the group consisting of agoraphobia, social phobia, panic attacks, panic disorders, simple phobia, mood disorders, major depression, schizophrenia, and hypermobility syndrome associated with duplication of a region of the genomic sequence of human chromosome 15q24-25 defined by boundaries D15S925 (proximal end) and DS15S736 (distal end), said method comprising identifying the presence of duplication in the region of the genomic sequence of human chromosome 15q24-25 defined by the boundaries D15S925 (proximal end) and DS15S736 (distal end) in said person.

2. A method for identifying a person at risk for developing anxiety disorder, said anxiety disorder selected from the group consisting of agoraphobia, social phobia, panic attacks, panic disorders, simple phobia, mood disorders, major depression, schizophrenia, and hypermobility syndrome associated with duplication of a region of the genomic sequence of human chromosome 15q24-25 defined by the boundaries D15S925 (proximal end) and DS15S736 (distal end), said method comprising a. providing a biological sample comprising genomic DNA from a patient suspected of having or at risk for developing said anxiety disorder; and b. using a probe to said region of the genomic sequence of human chromosome 15q24-25 defined by the boundaries D15S925 (proximal end) and DS15S736 (distal end) and c. detecting duplications in the region of the genomic sequence of human chromosome 15q24-25 defined by the boundaries D15S925 (proximal end) and DS15S736 (distal end).

3. The method according to claim 2 comprising using probes in a cellular assay based on fluorescent in situ hybridization (FISH).

4. The method according to claim 2 comprising using probes in a cytogenetic assay based on fluorescent is situ hybridization (FISH).

5. The method according to claim 1 comprising using an assay based on DNA or RNA analysis of genes of regions of human chromosome 15q24-25 inside of the boundaries D15S925 (proximal end) and DS15S736 (distal end).

\* \* \* \* \*